(12) United States Patent
De Hoyos Garza

(10) Patent No.: US 6,454,785 B2
(45) Date of Patent: Sep. 24, 2002

(54) PERCUTANEOUS INTRAGASTRIC BALLOON CATHETER FOR THE TREATMENT OF OBESITY

(76) Inventor: Andrés De Hoyos Garza, Mexico City (MX)

(*) Notice: Subject to any disclaimer, the term of this patent is extended or adjusted under 35 U.S.C. 154(b) by 14 days.

(21) Appl. No.: 09/792,234

(22) Filed: Feb. 23, 2001

(30) Foreign Application Priority Data

Feb. 24, 2000 (MX) .............................................. 001922

(51) Int. Cl.⁷ .............................................. A61M 29/00
(52) U.S. Cl. ...................... 606/192; 606/191; 606/193; 606/194; 606/195; 606/196; 606/197; 606/198; 604/96; 604/97; 604/98; 604/99; 604/101
(58) Field of Search .............................. 606/191, 192, 606/193, 194, 195, 196, 197, 198, 220; 604/96, 97, 98, 99, 100, 101

(56) References Cited

U.S. PATENT DOCUMENTS

| | | |
|---|---|---|
| 2,687,131 A | 4/1954 | Raiche |
| 4,057,065 A | 11/1977 | Thow |
| 4,133,315 A | 1/1979 | Berman et al. |
| 4,246,893 A | 1/1981 | Berson |
| 4,315,513 A | 2/1982 | Nawash et al. |
| 4,416,267 A | 11/1983 | Garren et al. |
| 4,485,805 A | 12/1984 | Foster, Jr. |
| 4,624,657 A | 11/1986 | Gould et al. |
| 4,666,433 A | 5/1987 | Parks |
| 4,723,547 A | 2/1988 | Kullas et al. |
| 4,739,758 A | 4/1988 | Lai et al. |
| 4,861,334 A | 8/1989 | Nawaz |
| 4,899,747 A | 2/1990 | Garren et al. |
| 5,084,061 A | 1/1992 | Gau et al. |
| 5,234,454 A | 8/1993 | Bangs |
| 5,259,399 A | 11/1993 | Brown |
| 5,993,473 A | 11/1999 | Chan et al. |

*Primary Examiner*—A. Vanatta
*Assistant Examiner*—Robert H. Muromoto, Jr.
(74) *Attorney, Agent, or Firm*—Reising, Ethington, Barnes, Kisselle, Learman & McCulloch, P.C.

(57) ABSTRACT

The present invention relates to a percutaneous intragastric balloon catheter for the treatment of obesity. The invention occupies a portion of the gastric cavity causing a feeling of satiety and decreasing the consumption of food by an obese patient. This invention consists in a percutaneous intragastric balloon that is placed in a non-surgically form. The percutaneous intragastric balloon catheter is collocated by percutaneous endoscopic gastrotomy (PEG). The invention comprises an affixed valve for regulating the amount of fluid introduced or evacuated from the percutaneous intragastric balloon.

8 Claims, 4 Drawing Sheets

PERCUTANEOUS INTRAGASTRIC BALLOON CATHETER FOR THE TREATMENT OF OBESITY

FIELD OF THE INVENTION

This invention relates to gastrostomy devices for use in the treatment of obesity. More particularly, the invention relates to percutaneous balloon catheters positioned in the stomach for medical treatment of morbid obesity in humans.

BACKGROUND OF THE INVENTION

Morbid obesity is a chronic medical illness defined as overweight of 50 to 100 percent above the ideal body weight. Obesity is a major medical problem affecting millions of people worldwide. In addition to the phychosocial stigmas associated with the condition or disease, many serious health ramifications may develop. Hypertension, hyperlipidemia, exacerbation of diabetes mellitus, heart disease, degenerative arthritis, and Pickwickian syndrome. Certain types of cancer, gallstones, varicose veins, thromboembolism and hernias are more common among overweight individuals. In addition, morbid obesity can lead to psychosocial difficulties such as depression, loss of self-esteem and decreased employability.

To date, numerous attempts have been made to cause weight loss in morbidly obese patients. None of them have been entirely successful. The weight loss methods can be broadly divided into behavioral modification, vigorous exercise, use of pharmaceuticals, medical diets, surgical procedures and devices.

The recommended methods for weight loss are medical diets and behavioral modification. However, many persons are unable to achieve significant or sustained results using these methods because they depend solely upon the will-power of the patients. Sometimes vigorous exercise is recommended to achieve an increase in energy output. However many obese individuals risk further damage to their health from such activity (for example, heart attacks).

Another solution involves pharmaceuticals, their use may cause drawbacks such as the individual becoming addicted or ill-affected by side effects. Sometimes, these drugs become less potent over time due to the development of a high drug tolerance.

Surgical procedures for treatment of obesity include procedures that lead to weight loss by malabsorption such as jejunoileal or gastric bypass surgery, gastroplasty and gastric stapling and oral surgical procedures such as wiring shut the patient's jaws to reduce food intake. These procedures are usually quite effective in producing weight loss but some of them have been accompanied by serious complications and side effects, including operative mortality as high as three to six percent, postoperative wound infection, liver disfunction and failure, kidney stones, diarrhea and the need for further surgeries to treat intestinal obstruction or hernias, or to revise original surgery because of intolerable side effects.

In U.S. Pat. No. 4,133,315, Berman proposes placing a distensible device within the lumen of the stomach having a filling tube permanently extended up through the esophagus and out of the nasal cavity or out of the mouth. While this method basically assures retrieval of the balloon upon deflation, the extreme discomfort and major inconvenience for the patient with this method should be selfevident.

A surgical adjunct is described in U.S. Pat. No. 4,246,893. An inflatable balloon-like device is implanted surgically through an incision in the abdominal wall and the peritoneum into the upper abdomen and anterior to the stomach, reducing its capacity.

U.S. Pat. Nos. 4,416,267 and 4,899,747 of Garren et al., disclose an intragastric balloon which is discharged into the stomach through an orogastric introducer tube to provide satiety. However, spontaneous deflation of the balloon is possible and passage of the deflated device through the pylorus often results in small bowel obstruction which requires surgery. Also it is believed that the failure to show any significant increased weight loss may be caused by a high incidence of spontaneous balloon deflation. Furthermore this kind of adjunct presents the inconvenience of not regulating the volume of the balloon according to the results in weightless or gastric discomfort of the patient.

A similar device for weight loss is set forth in U.S. Pat. Nos. 4,485,805; 4,739,758 and 4,723,547 wherein a free-floating intragastric balloon is placed in the stomach. The intragastric balloon may be withdrawn by endoscopy using a loop that is placed on the balloon. It is believed that mucosal erosion and gastric ulceration in some patients are caused by the cylindrical shape of the device and the balloon edges.

Catheters are commonly used as providing nourishment and for gastrostomy tubes for the purpose of ravaging a patient's stomach. Such gastrostomy devices have been the subject of U.S. Pat. Nos. 4,315,513 and 4,666,433. The use of an inflatable balloon as part of the tube for holding it in place while feeding or lavaging is set forth in U.S. Pat. Nos. 4,624,657 and 4,861,334.

A similar device is presented in U.S. Pat. No. 2,687,131; the inflatable balloon is placed adjacent the drainage eyes of the catheter.

U.S. Pat. No. 4,057,065 presents the use of two balloons within a catheter: the gastrointestinal tube has an inflatable balloon within the stomach to decompress it. A second inflatable balloon is provided at the distal end of the tube which is threatened through the pylorus, jejunum and ligament of Trietz and into the small intestine where it may be inflated.

Gan et al., in U.S. Pat. No. 5,084,061 propose a free-floating intragastric balloon with a self-sealing valve, using an endoscope for inflating or deflating the balloon.

Bangs (U.S. Pat. No. 5,234,454), describes a fixation device employing nylon garment T-fasteners to affix the anterior gastric wall to the abdominal wall for percutaneous gastrostomy. Nevertheless the intragastric balloon catheter is placed with surgery.

U.S. Pat. No. 5,259,399 relates to a bladder being positioned into and withdrawn from the stomach through a percutaneous endoscopic gastrostomy tube permanently placed. The method for collocating the tube is very complex and elaborate.

Chan et al. (U.S. Pat. No. 5,993,473), mention a device that requires a gastro-cutaneous fistula established in the obese individual via a percutaneous endoscopic gastrostomy. The disadvantage is that the fistula track is allowed to mature over a long period of time, from 1 to 2 weeks.

Notwithstanding the above described art, there continues to be a need for a percutaneous intragastric balloon catheter which can be non-surgically placed in the lumen of the stomach with easy collocation consisting of just one step, of simple and low cost manufacture, with few collateral effects and that will provide satiety to a patient without significant risk of morbidity.

SUMMARY OF THE INVENTION

It is a first object of the invention to provide an improved percutaneous intragastric balloon catheter for the treatment of obesity.

It is a second object of the invention to provide an improved percutaneous intragastric balloon catheter which is easily introduced by Percutaneous Endoscopic Gastrostomy (PEG).

It is a third object of the invention to provide an improved percutaneous intragastric balloon catheter which has a low ulceration and erosion potencial.

It is a fourth object of the invention to provide an improved percutaneous intragastric balloon catheter which is prevented from moving and/or prevented from excessive movement while in the gastric cavity.

It is a fifth object of the invention to provide an improved percutaneous intragastric balloon catheter for the gastric cavity which is safe to use causing a feeling of satiety and that achieves less consumption of food by a patient.

It is a sixth object of the invention to provide an improved percutaneous intragastric balloon catheter having a low risk of small bowel obstruction or esophageal obstruction.

It is a seventh object of the invention to provide a percutaneous intragastric balloon catheter which comprises an affixed valve, which permits to regulate the volume (filling and emptying) of the percutaneous intragastric balloon since the placement procedure thorough the treatment.

In one aspect of the invention, a percutaneous intragastric balloon catheter is provided to cause weight loss in obese persons by occupying a portion of the stomach volume. The balloon catheter is positioned into the stomach through the "Pull" or "Push" technique, more especifically by Percutaneous Endoscopic Gastrostomy (PEG) and withdrawn by endoscopy, both are non-surgical procedures.

The balloon is filled to occupy a large portion of the stomach to cause a feeling of satiety and to decrease the consumption of food by an obese patient. The emptying of the balloon provides periods of reduced trauma to the stomach.

In another aspect of the invention, it is disclosed a medical device for treatment of obese patients comprising a percutaneous intragastric balloon, two anchors (internal and external), a fillant catheter, a valve, a detachable cover, a plastic membrane and a fillant device. The percutaneous intragastric balloon is shaped for occupying a portion of the stomach and is preferably constructed of a durable and biocompatible material, such as surgical grade latex rubber. Both anchors are present to provide suitable surfaces that prevent movement of the percutaneous intragastric balloon catheter while in the gastric cavity. The purpose of the fillant catheter, which is connected to said percutaneous intragastric balloon, is having means for filling and emptying the percutaneous intragastric balloon and as means for supporting both anchors and the valve. The above referenced system comprises a valve for controlling the amount of fluid introduced or evacuated from the percutaneous intragastric balloon through the fillant catheter. The detachable cover envelopes the extreme end of the valve, which connects with the fillant device, during the placement procedure of the percutaneous intragastric balloon catheter. The purpose of the plastic membrane is to envelop the percutaneous intragastric balloon, in its non-inflated position, facilitating its passage through the gastrointestinal tract while collocating the system. The fillant device is loaded with the appropriate amount of fluid for filling the percutaneous intragastric balloon.

DESCRIPTION OF THE PREFERRED EMBODIMENTS

Figure 1:
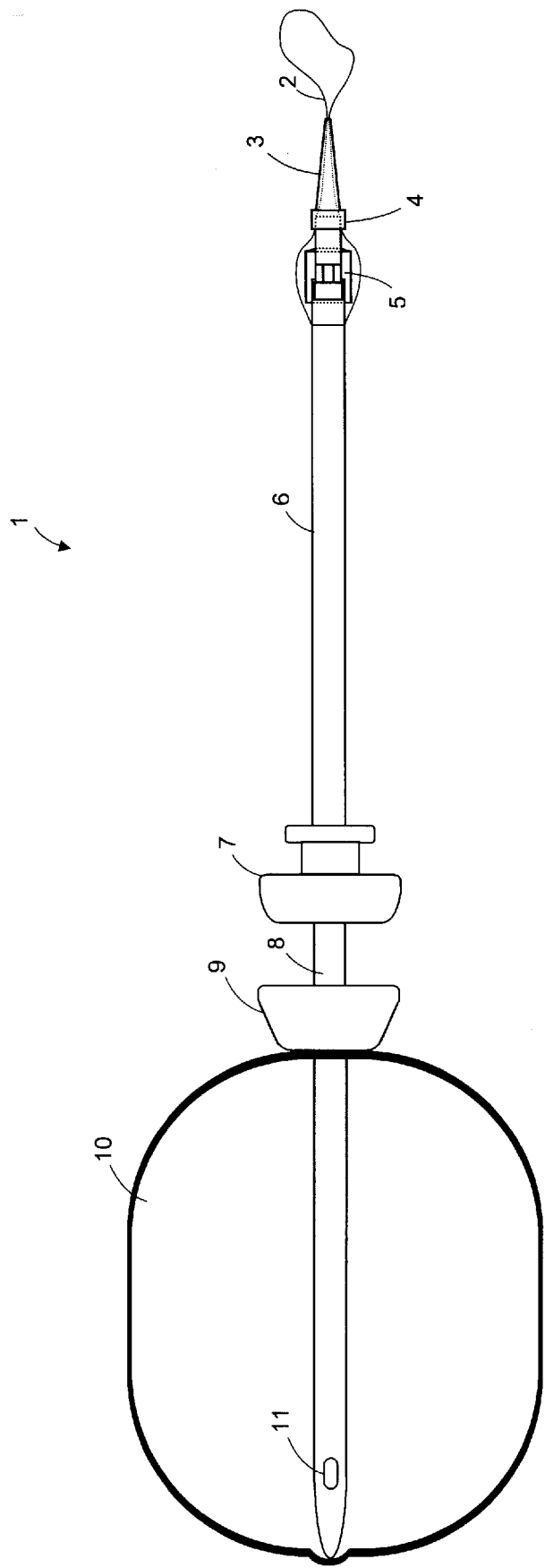
FIG. 1 shows a longitudinal cross-sectional view of the percutaneous intragastric balloon catheter in its inflated position according to the present invention.

With reference to FIG. 1, the present invention, the percutaneous intragastric balloon catheter, is depicted by the number 1. It comprises a non-rigid circular plastic fillant catheter 6 having a distal end that includes a slot 11, through which the fluid fills the percutaneous intragastric balloon 10, shown in its inflated position. The aforementioned fluid may be a gas, liquid, gel or a mixture thereof An internal anchor 9 is placed near the distal end of the fillant catheter to prevent excessive movement of the percutaneous balloon 10 while in the gastric cavity. As it can be appreciated in this figure, after internal anchor 9 there is a portion 8 of the fillant catheter. This portion 8 trespasses the abdominal wall. The external anchor 7 has the purpose of securing the percutaneous intragastric balloon 10 to the outside flank of the abdominal wall. On the proximal end of the fillant catheter 6 there is a valve 5 for allowing the fillant fluid to be introduced and evacuated from the fillant catheter 6. The purpose of detachable cover 3 is to envelop the extreme end of the valve 5, where the fillant device 13 (FIG. 4) is connected, during the placement procedure (FIG. 2) and to facilitate the passage of the valve 5 and fillant catheter 6 through the tiny incision on the skin made by a needle, as described in FIG. 2. On the surface of the valve 5 and underneath the detachable cover 3, a filament or thread 2 is positioned as means for attaching the guidewire 15 (FIG. 2) during the process of collocation.

Figure 2:
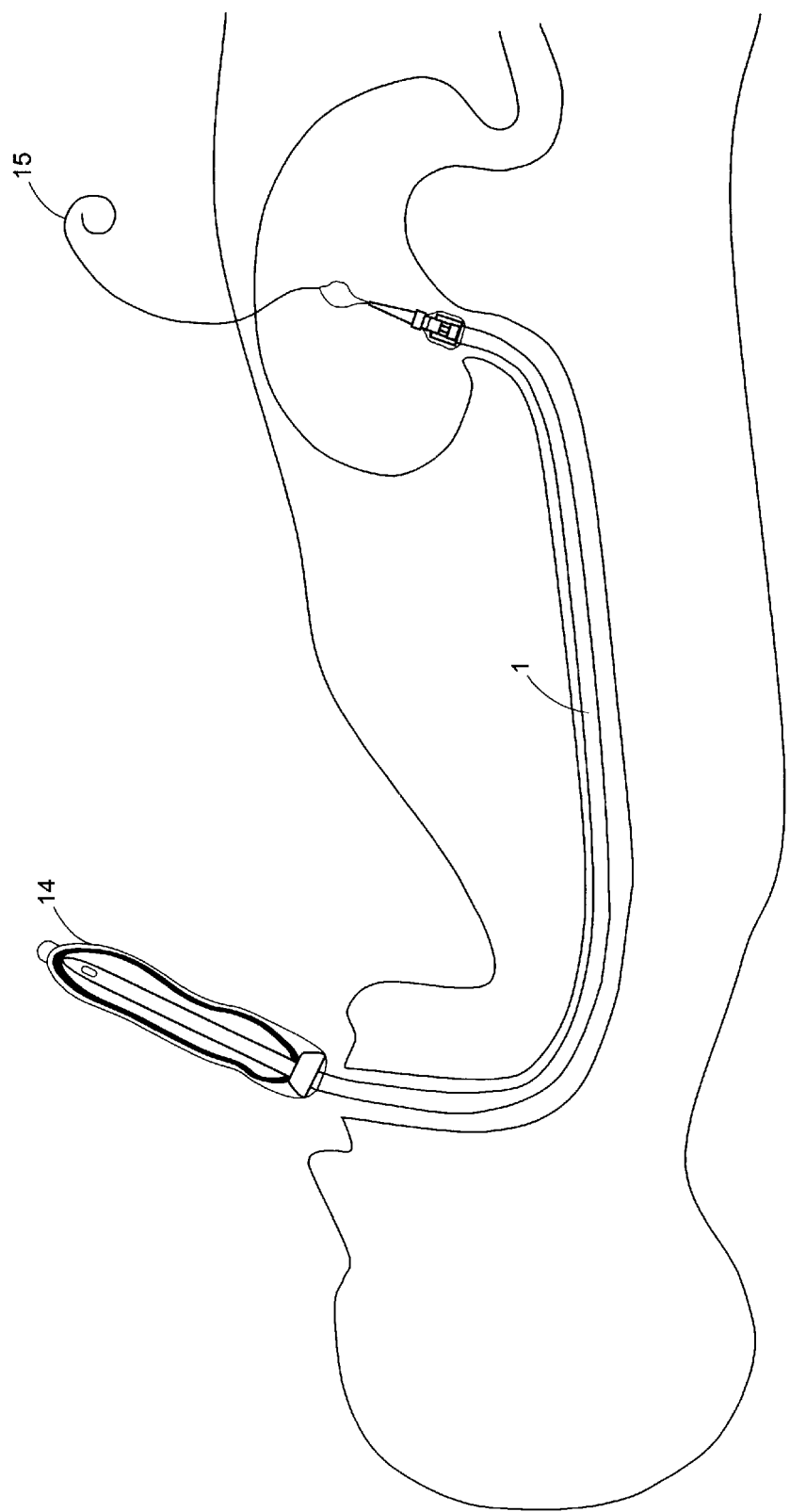
FIGS. 2 and 3 show the placement procedure for the percutaneous intragastric balloon catheter.
Figure 3:
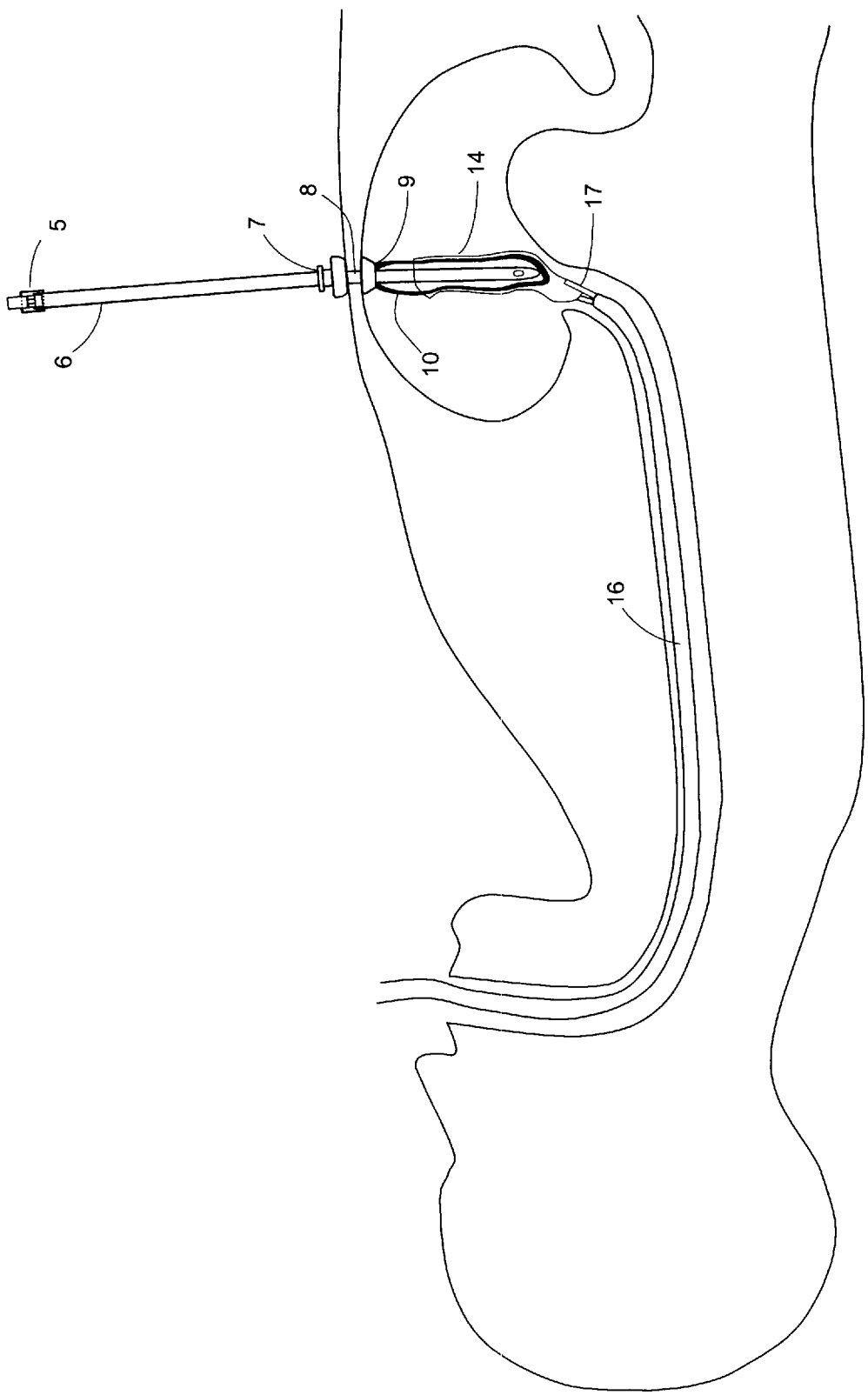

FIGS. 2 and 3 show the placement procedure, and function of the components of the percutaneous intragastric balloon catheter, that include: inspecting with an endoscope 16 the lumen of the stomach of the obese person. The endoscope 16 is introduced through the mouth down the esophagus into the stomach, with a needle puncturing the abdominal wall 12, through this puncture in the abdominal wall inserting the guidewire 15 from the outside into the fundus of the stomach, and grasping with the endoscope 16 the said guidewire 15. Extracting one end of the guidewire 15 by pulling the endoscope 16 out of the mouth while the other end of the guidewire 15 still remains outside of the abdomen 12. The percutaneous intragastric balloon catheter 1 is placed through the abdominal wall 12 by attaching the filament or thread 2 of the percutaneous intragastric balloon catheter 1 to the guidewire 15 extended out of the patient's mouth and pulling on the other end of the guidewire 15 until the filament or thread 2 of the percutaneous intragastric balloon catheter 1 is pulled through the puncture opening in the abdominal wall 12. The placed percutaneous intragastric balloon catheter 1 is secured on the stomach wall with the internal anchor 9, then the external anchor 7 is collocated through the proximal end, after the procedure of Percutaneous Endoscopic Gastrostomy (PEG), further securing the medical device 1 on the abdominal wall. As it can be seen in both figures, a plastic membrane 14 is covering the percutaneous intragastric balloon catheter 1. This membrane 14 has the function of compacting the percutaneous intragastric balloon, also the membrane 14 can be covered with a biocompatible lubricant to facilitate the passage through the mouth, esophagus and stomach. After the placement procedure, the membrane 14 is removed (FIG. 3) using biopsy clamps 17 attached to an endoscope 16.

Figure 4:
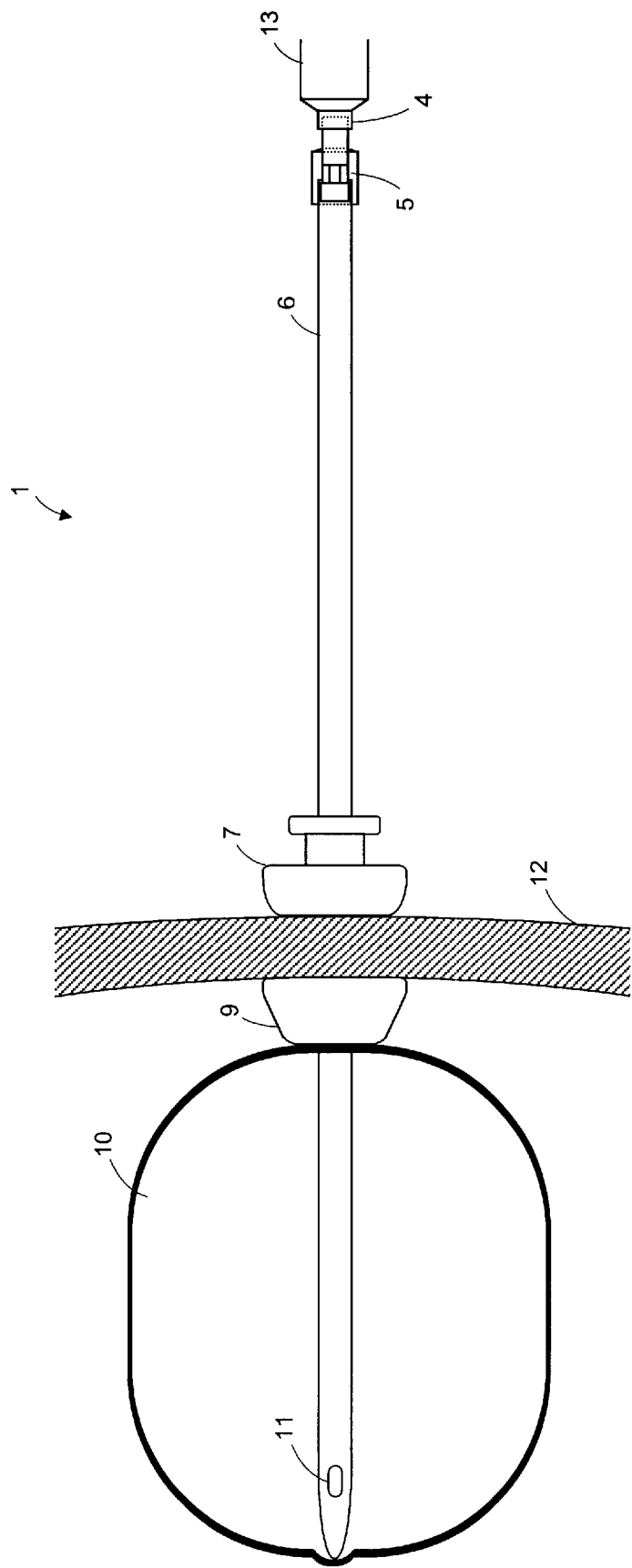
FIG. 4 shows a partial longitudinal cross-sectional view of the percutaneous intragastric balloon catheter within the gastric cavity of a person.

FIG. 4 shows the percutaneous intragastric balloon catheter 1 as it is collocated within the gastric cavity of a person. In this figure, it can be appreciate that the percutaneous intragastric balloon 10, in its inflated position, has a smooth surface to prevent gastric erosion. Anchors 7 and 9 are holding the percutaneous intragastric balloon catheter 1 attached to the abdominal wall 12 preventing accidental withdrawal of the percutaneous intragastric balloon associated with deflation and passage of the above mentioned balloon into the small bowel and esophagus. Valve 5 is connected with the fillant device 13 that provides an adequate amount of fluid for filling the percutaneous intragastric balloon 10, as it can be observed in the schematic representation. Fillant device 13 may be a pump or a hypodermic syringe that forces the fluid in and out of the percutaneous intragastric balloon 10.

Based upon the foregoing disclosure, certain embodiments and details have been described for the purpose of illustrating the present invention, it will be apparent to those skilled in the art that variations and modifications may be made without departing from the scope of the invention.

What is claimed is:

1. A percutaneous intragastric balloon catheter for the treatment of obesity that occupies a segment of the stomach volume, said catheter comprising:

a percutaneous intragastric balloon shaped for occupying a portion of the gastric cavity;

a fillant catheter connected to said percutaneous intragastric balloon for repeated filling and emptying with a fluid and as means for supporting two anchors and a valve;

two anchors, external and internal, for providing suitable surfaces that prevent movement of the percutaneous intragastric balloon catheter while in the gastric cavity;

a valve for controlling the amount of fluid introduced or evacuated from the percutaneous intragastric balloon through the fillant catheter;

a conically shaped detachable cover that envelopes the extreme end of the valve, which connects with the fillant device, during the placement procedure; and, a fillant device that is loaded with the appropriate amount of fluid for filling the percutaneous intragastric balloon.

2. The percutaneous intragastric balloon catheter of claim 1, wherein said percutaneous intragastric balloon, in its non-inflated position, is covered with a plastic membrane during the placement procedure.

3. The percutaneous intragastric balloon catheter of claim 1, wherein said percutaneous intragastric balloon has a smooth surface and is constructed of a durable and biocompatible material.

4. The percutaneous intragastric balloon catheter of claim 1, wherein said fillant catheter is non-rigid, circular and made of a plastic material.

5. The percutaneous intragastric balloon catheter of claim 1, wherein said fluid is a gas, liquid, gel or a mixture thereof.

6. The percutaneous intragastric balloon catheter of claim 1, wherein a filament or thread is positioned on the surface of said valve and underneath said detachable cover as means for facilitating the placement procedure.

7. The percutaneous intragastric balloon catheter of claim 1, wherein said external collocated on the abdominal wall after the placement procedure.

8. The percutaneous intragastric balloon catheter of claim 1, wherein said fillant device is a pump or a hypodermic syringe.

* * * * *